(12) United States Patent
Chow

(10) Patent No.: US 8,280,500 B2
(45) Date of Patent: Oct. 2, 2012

(54) DISCRIMINATION OF VENTRICULAR TACHYCARDIA FROM SUPRAVENTRICULAR TACHYCARDIA

(75) Inventor: Theodore Chow, Saratoga, CA (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

(21) Appl. No.: 12/476,811

(22) Filed: Jun. 2, 2009

(65) Prior Publication Data
US 2009/0299205 A1 Dec. 3, 2009

Related U.S. Application Data

(60) Provisional application No. 61/130,604, filed on Jun. 2, 2008.

(51) Int. Cl.
*A61B 5/0464* (2006.01)
(52) U.S. Cl. .................................................. 600/518
(58) Field of Classification Search .................. 600/518
See application file for complete search history.

(56) References Cited

U.S. PATENT DOCUMENTS

| | | |
|---|---|---|
| 4,880,005 A | 11/1989 | Pless et al. |
| 5,002,052 A | 3/1991 | Haluska |
| 5,243,980 A | 9/1993 | Mehra |
| 5,325,856 A | 7/1994 | Nitzsche et al. |
| 5,327,900 A | 7/1994 | Mason et al. |
| 5,379,776 A | 1/1995 | Murphy et al. |
| 5,404,880 A | 4/1995 | Throne |
| 5,411,530 A | 5/1995 | Akhtar |
| 5,591,215 A | 1/1997 | Greenhut et al. |
| 5,620,471 A | 4/1997 | Duncan |
| 5,622,178 A | 4/1997 | Gilham |
| 5,868,793 A | 2/1999 | Nitzsche et al. |
| 5,882,352 A | 3/1999 | Duncan et al. |
| 5,941,831 A | 8/1999 | Turcott |
| 5,978,700 A | 11/1999 | Nigam |
| 6,035,232 A | 3/2000 | Thong et al. |
| 6,167,308 A | 12/2000 | DeGroot |
| 6,330,477 B1 | 12/2001 | Casavant |
| 6,567,691 B1 | 5/2003 | Stadler |
| 6,611,713 B2 | 8/2003 | Schauerte |
| 6,748,269 B2 | 6/2004 | Thompson et al. |
| 6,980,860 B2 | 12/2005 | Stadler et al. |
| 7,031,765 B2 | 4/2006 | Ritscher et al. |
| 7,146,215 B1 | 12/2006 | Mo |

(Continued)

FOREIGN PATENT DOCUMENTS

EP 0 597 459 A2 5/1994

OTHER PUBLICATIONS

European Response filed on Mar. 7, 2011 for corresponding European Patent Application No. 09759235.6 (3 pages).

(Continued)

*Primary Examiner* — Eric D. Bertram
(74) *Attorney, Agent, or Firm* — Shumaker & Sieffert, P.A.

(57) ABSTRACT

This disclosure describes various techniques for discriminating supraventricular tachycardia (SVT) from ventricular tachycardia (VT). As one example, a method includes detecting a tachycardia rhythm, identifying a rate of change in heart rate corresponding to the tachycardia rhythm, identifying a rate of change in heart rate variability corresponding to the tachycardia rhythm, and classifying the tachycardia rhythm as at least one of supraventricular tachycardia or ventricular tachycardia based on the rate of change in heart rate and rate of change in heart rate variability.

22 Claims, 15 Drawing Sheets

U.S. PATENT DOCUMENTS

| | | | |
|---|---|---|---|
| 7,149,577 | B2 | 12/2006 | Sharma et al. |
| 7,203,535 | B1 | 4/2007 | Hsu et al. |
| 7,313,438 | B2 | 12/2007 | Zhang |
| 7,317,942 | B2 | 1/2008 | Brown |
| 7,353,057 | B2 | 4/2008 | Schiessle et al. |
| 7,756,578 | B2 * | 7/2010 | Kim et al. ............. 607/14 |
| 2003/0109792 | A1 | 6/2003 | Hsu et al. |
| 2005/0154421 | A1 | 7/2005 | Ousdigian |
| 2006/0089675 | A1 | 4/2006 | Burnes et al. |
| 2006/0217769 | A1 | 9/2006 | Saba |
| 2008/0004666 | A1 | 1/2008 | Schauerte |
| 2008/0269819 | A1 | 10/2008 | Zhou |
| 2009/0099616 | A1 * | 4/2009 | Li et al. ............. 607/17 |

OTHER PUBLICATIONS

Lee A. Fleisher, MD, "Heart Rate Variability as an Assessment of Cardiovascular Status," *Journal of Cardiothoracic and Vascular Anesthesia*, vol. 10, No. 5 Aug. 1996, pp. 659-671.

I Ungi et al., "Investigation of the Correlation Between Heart Rate and Heart Rate Variability," *Computers in Cardiology*, 1995, pp. 189-191.

International Search Report and Written Opinion from corresponding PCT Application Serial No. PCT/US2009/045959 mailed Aug. 13, 2009 (16 pages).

Robert Arzbaecher et al., "Automatic Tachycardia Recognition," Pacing and Clinical Electrophysiology, vol. 7, No. 3, Part II, pp. 541-547 (May 1984).

Janice Jenkins et al., "A Single Atrial Extrastimulus Can Distinguish Sinus Tachycardia from 1:1 Paroxysmal Tachycardia," Pacing and Clinical Electrophysiology, vol. 9, No. 6, Part II, pp. 1063-1068 (Nov. 1986).

Response to Written Opinion from corresponding PCT Application Serial No. PCT/US2009/045959 filed on Apr. 2, 2010 (12 pages).

International Preliminary Report on Patentability from corresponding PCT Application Serial No. PCT/US2009/045959 dated Sep. 14, 2009 (17 pages).

* cited by examiner

DISCRIMINATION OF VENTRICULAR TACHYCARDIA FROM SUPRAVENTRICULAR TACHYCARDIA

This application claims the benefit of U.S. Provisional Application No. 61/130,604, to Chow, entitled, "ADDITIONAL METHODS FOR DISCRIMINATION OF VT FROM SVT," and filed on Jun. 2, 2008, the entire content of which is incorporated herein by reference.

TECHNICAL FIELD

This disclosure relates to implantable medical devices and, more particularly, implantable medical devices that detect tachycardia.

BACKGROUND

Medical devices, such as cardiac pacemakers, cardiac defibrillators, or implantable cardioverter-defibrillators, provide therapeutic electrical stimulation to a heart of a patient via electrodes carried by one or more medical leads and/or electrodes on a housing of the medical device. The electrical stimulation may include signals such as pulses or shocks for pacing, cardioversion or defibrillation. In some cases, a medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm of the heart. For example, in some cases, an implantable medical device (IMD) or an external medical device may deliver pacing pulses to the heart of the patient upon detecting tachycardia or bradycardia or deliver cardioversion or defibrillation shocks to the heart upon detecting tachycardia or fibrillation.

In general, medical devices detect tachycardia or fibrillation of the atria or ventricles based on the intervals between depolarizations, which are a function of the rate of the depolarizations. Accordingly, in some examples, a medical device detects a ventricular tachycardia of the intervals between ventricular depolarizations are less than a first threshold, and ventricular fibrillation of the intervals between ventricular depolarizations are less than a second threshold. Other features, such as rate variability or electrogram morphology, have been used to classify or distinguish various types of arrhythmias.

In some cases, a fast ventricular depolarization rate may be the result of a sinus tachycardia or an atrial tachyarrhythmia, and is referred to as a supraventricular tachycardia. Delivery of therapy to the ventricles, such as a cardioversion or defibrillation pulse, in response to a supraventricular tachycardia will likely be ineffective and is undesired. Some medical devices distinguish between ventricular and supraventricular tachycardias by comparison of the rates of or intervals between depolarizations of the ventricles and atria. However, such comparisons may not effectively distinguish ventricular tachycardias from supraventricular tachycardias in all cases. For example, where both the atrial and ventricular depolarizations are rapid and have a substantially 1:1 correspondence, the cause may by a supraventricular tachycardia or a ventricular tachycardia with retrograde conduction to the atria.

SUMMARY

In general, this disclosure describes various techniques for discriminating supraventricular tachycardia (SVT) from ventricular tachycardia (VT). Examples include monitoring a result in one of the atria or ventricles of a stimulation pulse delivered to the other of the atria or ventricles, applying knowledge of retrograde and antegrade conduction of the heart gathered prior to an arrhythmia, e.g., during normal sinus rhythm, or considering rate of change of heart rate and heart variability during onset of the tachyarrhythmia. In some examples, when the ventricular rate is near a lower bound of a ventricular tachycardia threshold and classification of the rate is consistent with sinus tachycardia or another supraventricular tachycardia, the lower bound of the ventricular tachycardia zone is increased to avoid detection of ventricular tachycardia. These techniques may be advantageously employed in a medical device, such as an implantable cardioverter defibrillator to avoid delivering inappropriate therapy to the ventricles and/or to deliver appropriate therapy to the atria.

In one example, the disclosure is directed toward a method comprising detecting a tachycardia rhythm, identifying a rate of change in heart rate corresponding to the tachycardia rhythm, identifying a rate of change in heart rate variability corresponding to the tachycardia rhythm, and classifying the tachycardia rhythm as at least one of supraventricular tachycardia or ventricular tachycardia based on the rate of change in heart rate and rate of change in heart rate variability.

In another example, the disclosure is directed toward a system comprising a sensor that senses activity of a heart of a patient and a processor that detects a tachycardia rhythm based on the sensed activity, identifies a rate of change in heart rate corresponding to the tachycardia rhythm, identifies a rate of change in heart rate variability corresponding to the tachycardia rhythm, and classifies the tachycardia rhythm as at least one of supraventricular tachycardia or ventricular tachycardia based on the rate of change in heart rate and rate of change in heart rate variability.

In another example, the disclosure is directed toward a system comprising means for detecting a tachycardia rhythm, means for identifying a rate of change in heart rate corresponding to the tachycardia rhythm, means for identifying a rate of change in heart rate variability corresponding to the tachycardia rhythm, and means for classifying the tachycardia rhythm as at least one of supraventricular tachycardia or ventricular tachycardia based on the rate of change in heart rate and rate of change in heart rate variability.

In another example, the disclosure is directed toward a method comprising recording heart rate data for a patient over a period of time, recording heart rate variability data for the patient over the period of time, identifying a relationship between heart rate and heart rate variability for the patient based on the recorded data, subsequently detecting a tachycardia rhythm in the patient, and classifying the tachycardia rhythm as at least one of supraventricular tachycardia or ventricular tachycardia based on the relationship.

In another example, the disclosure is directed toward a system comprising a sensor that senses activity of a heart of a patient and a processor that records heart rate data for the patient over a period of time based on the sensed activity, records heart rate variability data for the patient over the period of time based on the sensed activity, identifies a relationship between heart rate and heart rate variability for the patient based on the recorded data, subsequently detects a tachycardia rhythm in the patient based on the sensed activity, and classifies the tachycardia rhythm as at least one of supraventricular tachycardia or ventricular tachycardia based on the relationship.

In another example, the disclosure is directed toward a system comprising means for recording heart rate data for a patient over a period of time, means for recording heart rate variability data for the patient over the period of time, means for identifying a relationship between heart rate and heart rate variability for the patient based on the recorded data, means for subsequently detecting a tachycardia rhythm in the patient, and means for classifying the tachycardia rhythm as at least one of supraventricular tachycardia or ventricular tachycardia based on the relationship.

The details of one or more examples are set forth in the accompanying drawings and the description below. Other features, objects, and advantages will be apparent from the description and drawings, and from the claims.

DETAILED DESCRIPTION

Figure 1:
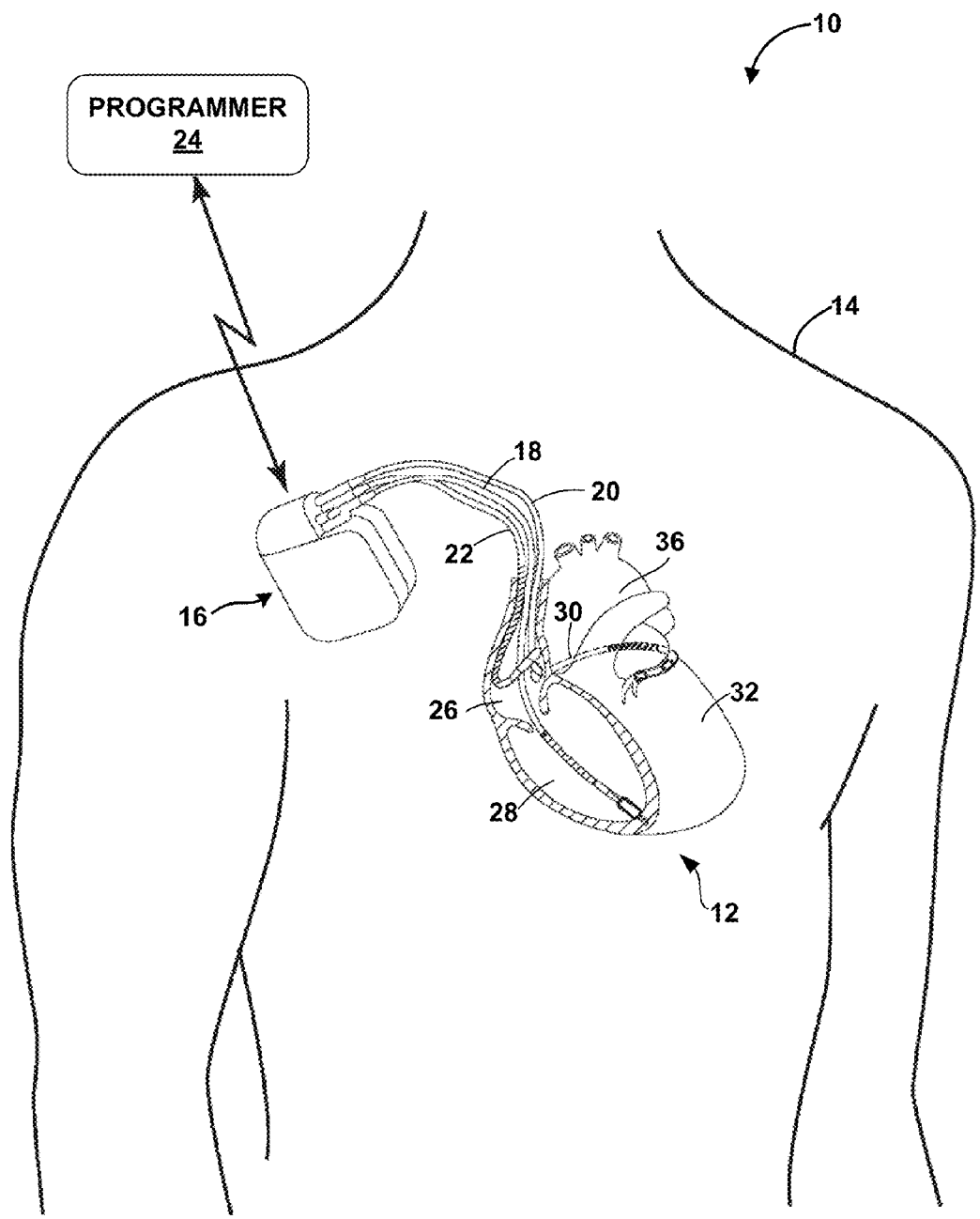
FIG. 1 is a conceptual diagram illustrating an example therapy system comprising an implantable medical device (IMD) that may be used to monitor one or more physiological parameters of a patient and/or provide therapy to the heart of a patient.

In general, this disclosure describes various techniques for discriminating supraventricular tachycardia (SVT) from ventricular tachycardia (VT). These techniques may be performed in an implantable medical device (IMD), such as an implantable pacemaker, defibrillator, cardioverter, or any combination thereof. An IMD will be described herein for purposes of example. Although, in other examples, these discrimination techniques may be performed by an external device, e.g., an external programmer that communicates with an IMD.

In one example, a processor, e.g., of an IMD, detects a tachycardia rhythm based on sensed cardiac activity and classifies the tachycardia as a 1:1 tachycardia, i.e., exhibiting one atrial complex per one ventricular complex. The IMD may deliver a pacing pulse to an atrium of the patient timed to be substantially synchronous with a ventricular depolarization. For example, the IMD may predict the timing of the ventricular depolarization based on sensed cardiac activity preceding the ventricular depolarization, e.g., based on the timing of previously sensed ventricular depolarizations, and deliver the pacing pulse at the predicted time of the ventricular depolarization. As another example, the IMD may detect the ventricular depolarization based on sensed cardiac activity and deliver the pacing pulse in response to the detected ventricular depolarization. In this manner, the IMD may deliver the pacing pulse while the ventricular depolarization is underway or just after the detected ventricular depolarization and prior to a subsequent atrial depolarization.

In the case of VT, the antegradely conducting atrial depolarization traveling from the atrium to the ventricle induced by the pacing pulse may collide with the retrogradely conducting depolarization traveling from the ventricle to the atrium corresponding to the VT, e.g., in the atrioventricular (AV) node or His-purkinje system. Thus, the propagation of the atrial depolarization induced by the pacing pulse may be prevented by the opposing retrogradely conducting depolarization corresponding to the VT. Therefore, the atrial depolarization induced by the pacing pulse may not perturb the VT. The next atrial and ventricular depolarizations may occur at predicted times, e.g., consistent with the timing of detected atrial and ventricular depolarizations preceding the pacing pulse.

In the case of SVT, e.g., atrial tachycardia or sinus tachycardia, the pacing pulse may reset the tachycardia and the next atrial and ventricular depolarizations may not occur at the predicted times, e.g., may be inconsistent with the timing of detected atrial and ventricular depolarizations preceding the pacing pulse. For example, the subsequent atrial and ventricular depolarizations may more closely resemble normal sinus rhythm.

As another example, the IMD may deliver a pacing pulse to a ventricle of the patient timed to be substantially synchronous with an atrial depolarization, e.g., upon detecting a 1:1 tachycardia. The IMD may trigger the pacing pulse when a ventricular depolarization is predicted to occur, e.g., based on the timing of previously detected atrial depolarizations. As another example, the IMD may detect the atrial depolarization and deliver the pacing pulse in response to the detected atrial depolarization.

In the case of SVT, the antegradely conducting spontaneous depolarization traveling from the atrium to the ventricle may collide with the retrogradely conducting depolarization traveling from the ventricle to the atrium induced by the pacing pulse, e.g., in the AV node or His-purkinje system, and the next atrial and ventricular depolarizations may occur at predicted times, e.g., consistent with the timing of detected atrial and ventricular depolarizations preceding the pacing pulse. In the case of VT, the pacing pulse may reset the tachycardia and the next atrial and ventricular depolarizations may not occur at the predicted times, e.g., may be inconsistent with the timing of detected atrial and ventricular depolarizations preceding the pacing pulse.

Other discrimination techniques may also be used. For example, the presence and/or absence of antegrade and/or retrograde conduction prior to a detected 1:1 tachycardia may be used to distinguish SVT from VT. A 1:1 SVT may be associated with antegrade conduction and, thus, a lack of antegrade conduction determined prior to a 1:1 tachycardia may signify that the 1:1 tachycardia is a VT. Likewise, a 1:1 VT may be the result of retrograde conduction and, thus, a lack of retrograde conduction determined prior to a 1:1 tachycardia may signify that a detected 1:1 tachycardia is an SVT.

Heart rate and heart rate variability information may additionally or alternatively be used to discriminate SVT from VT. A rate of change in heart rate and rate of change of heart rate variability associated with a tachycardia rhythm may be used to classify the tachycardia as SVT or VT, since SVT and VT may be associated with different patterns of change in these parameters.

As another example, a patient's heart rate and heart rate variability may be recorded over time. A patient-specific relationship between heart and heart rate variability may be determined based on the recorded data. When a tachycardia rhythm is subsequently detected, a medical device may determine whether the detected heart rate and associated heart rate variability conform to the extrapolated relationship. A tachycardia rhythm that follows that relationship or within a tolerance of the relationship may be classified as SVT, while a tachycardia rhythm falling outside a tolerance of the relationship may be classified as VT.

Discriminating SVT from VT may be useful in determining the appropriate response to a detected tachycardia rhythm. For example, VT may be more serious than SVT and require a more aggressive response. For example, a medical device may deliver anti-tachycardia therapy configured to treat VT upon its detection. Whereas, upon detection of SVT, a medical device may deliver less aggressive therapy or simply monitor the status of the tachycardia rhythm. Furthermore, therapy may be delivered to the ventricles to treat VT, or to the atria to treat an SVT.

FIG. 1 is a conceptual diagram illustrating an example therapy system 10 that may be used to monitor one or more physiological parameters of patient 14 and/or to provide therapy to heart 12 of patient 14. Therapy system 10 includes IMD 16, which is coupled to leads 18, 20, and 22, and programmer 24. IMD 16 may be an implantable pacemaker that provides electrical signals to heart 12 via electrodes coupled to one or more of leads 18, 20, and 22. In some examples, IMD 16 may also include cardioversion and/or defibrillation functionalities. Patient 12 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. RV lead 18 may be used for RV sensing and/or pacing of heart 12.

Left ventricular (LV) lead 20 extends through one or more veins, the vena cava, right atrium 26, and into the coronary sinus 30 to a region adjacent to the free wall of left ventricle 32 of heart 12. LV lead 20 may be used for LV sensing and/or pacing of heart 12. Right atrial (RA) lead 22 extends through one or more veins and the vena cava, and into the right atrium 26 of heart 12. RA lead 22 may be used for RA sensing and/or pacing. In some alternative examples, therapy system 10 may include an additional lead or lead segment (not shown in FIG. 1) that deploys one or more electrodes within the vena cava or other vein, or within or near the aorta.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The electrical signals sensed within heart 12 may also provide an indication of heart rate, heart rate variability, autonomic tone, and other indicators that may be used to distinguish SVT from VT. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art. IMD 16 may similarly deliver anti-tachycardia pacing or cardioversion in response to detecting tachycardia of ventricles 28 and 32.

In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, or other clinician, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14 or information derived from sensed physiological parameters, such as an indication tachycardia classification or one or more indicators that may be used to distinguish SVT from VT, e.g., heart rate and/or heart rate variability. As another example, the user may use programmer 24 to retrieve information from IMD 16 regarding the performance or integrity of IMD 16 or other components of system 10, such as leads 18, 20 and 22, or a power source of IMD 16. As another example, the user may interact with programmer 24 to program, e.g., select parameters for, therapies provided by IMD 16, such as pacing and, optionally, cardioversion and/or defibrillation.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
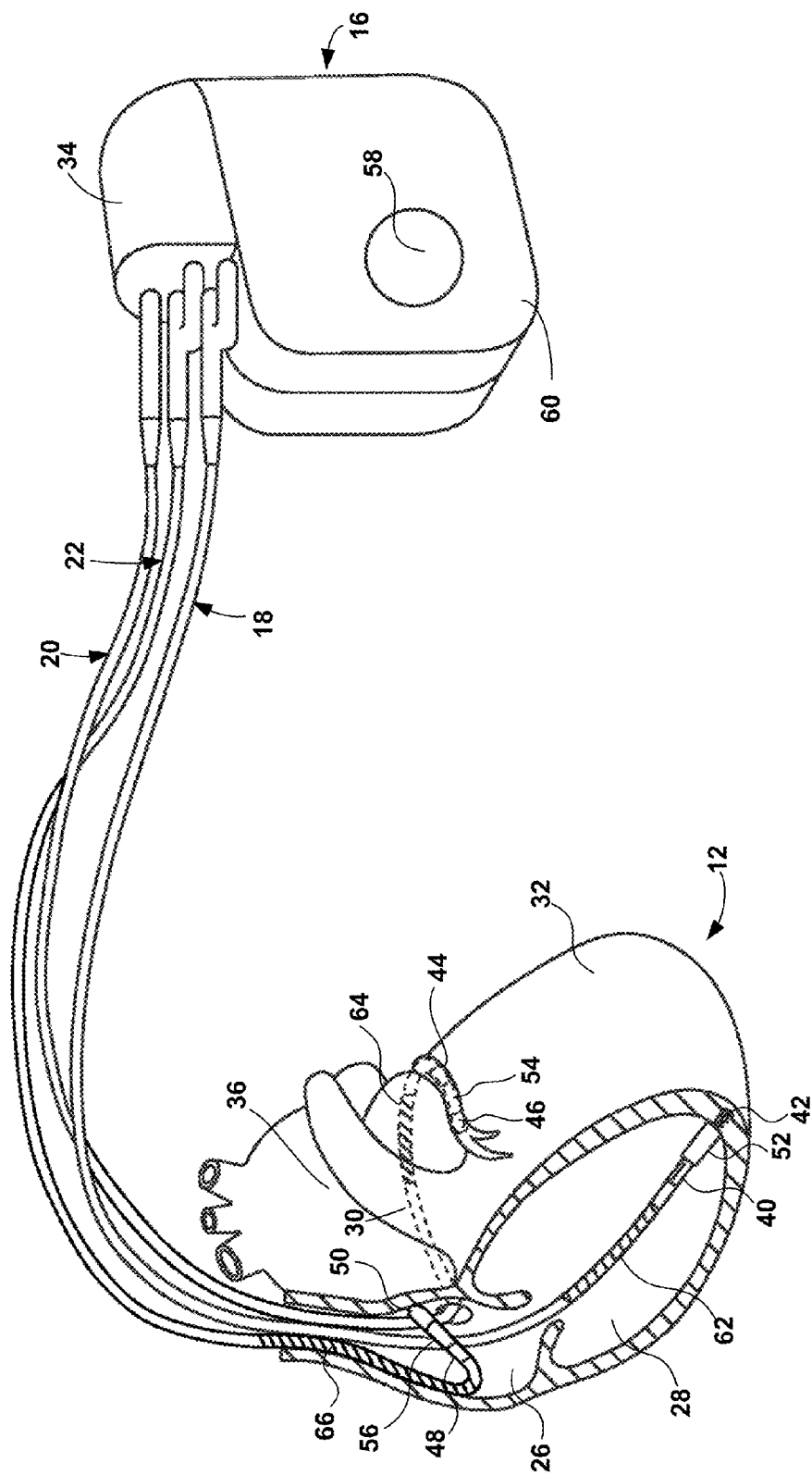
FIG. 2 is a conceptual diagram further illustrating the IMD and leads of the system of FIG. 1 in conjunction with the heart.

FIG. 2 is a conceptual diagram illustrating IMD 16 and leads 18, 20, 22 of therapy system 10 in greater detail. Leads 18, 20, 22 may be electrically coupled to a signal generator and an electrical sensing module of IMD 16 via connector block 34. Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36, but other examples may include electrodes in left atrium 36. Furthermore, other examples may include electrodes in other locations, such as the aorta, subclavian vein, or a vena cava, or epicardial or extracardial electrodes proximate to any of the chambers or vessels described herein.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other embodiments, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as an electrical sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. For example, electrodes 40, 42, and/or 58 may be used to deliver RV pacing to heart 12. Additionally or alternatively, electrodes 44, 46, and/or 58 may be used to deliver LV pacing to heart 12, and electrodes 48, 50 and/or 58 may be used to deliver RA pacing to heart 12.

Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. It should be understood that various other electrode and lead configurations are within the scope of this disclosure. For example, a therapy system may include epicardial leads and/or patch electrodes instead of or in addition to the transvenous leads 18, 20, 22 illustrated in FIG. 1.

In some examples, leads 18, 20, 22 may include other electrodes in addition to those shown in FIG. 2. Additional electrodes may be used for sensing and may provide additional vectors, e.g., for the analysis of the morphology of tachycardia or other arrhythmias. For example, additional electrodes may be provided in right atrium 26, left atrium 36, the right subclavian vein and/or the left subclavian vein. Additional electrodes may provide unique vectors that may be used in conjunction with other standard vectors to provide a more three-dimensional visualization of electrogram morphology.

In addition, in other examples, a therapy system may include any suitable number of leads coupled to IMD 16, and each of the leads may extend to any location within or proximate to heart 12. Other examples of therapy systems may include three transvenous leads located as illustrated in FIGS. 1 and 2, and an additional lead located within or proximate to left atrium 36. Additional examples of therapy systems may include a single lead that extends from IMD 16 into right ventricle 28, or two leads that extend into a respective one of the right ventricle 26 and right atrium 26. An example of this type of therapy system is shown in FIG. 3.

Figure 3:
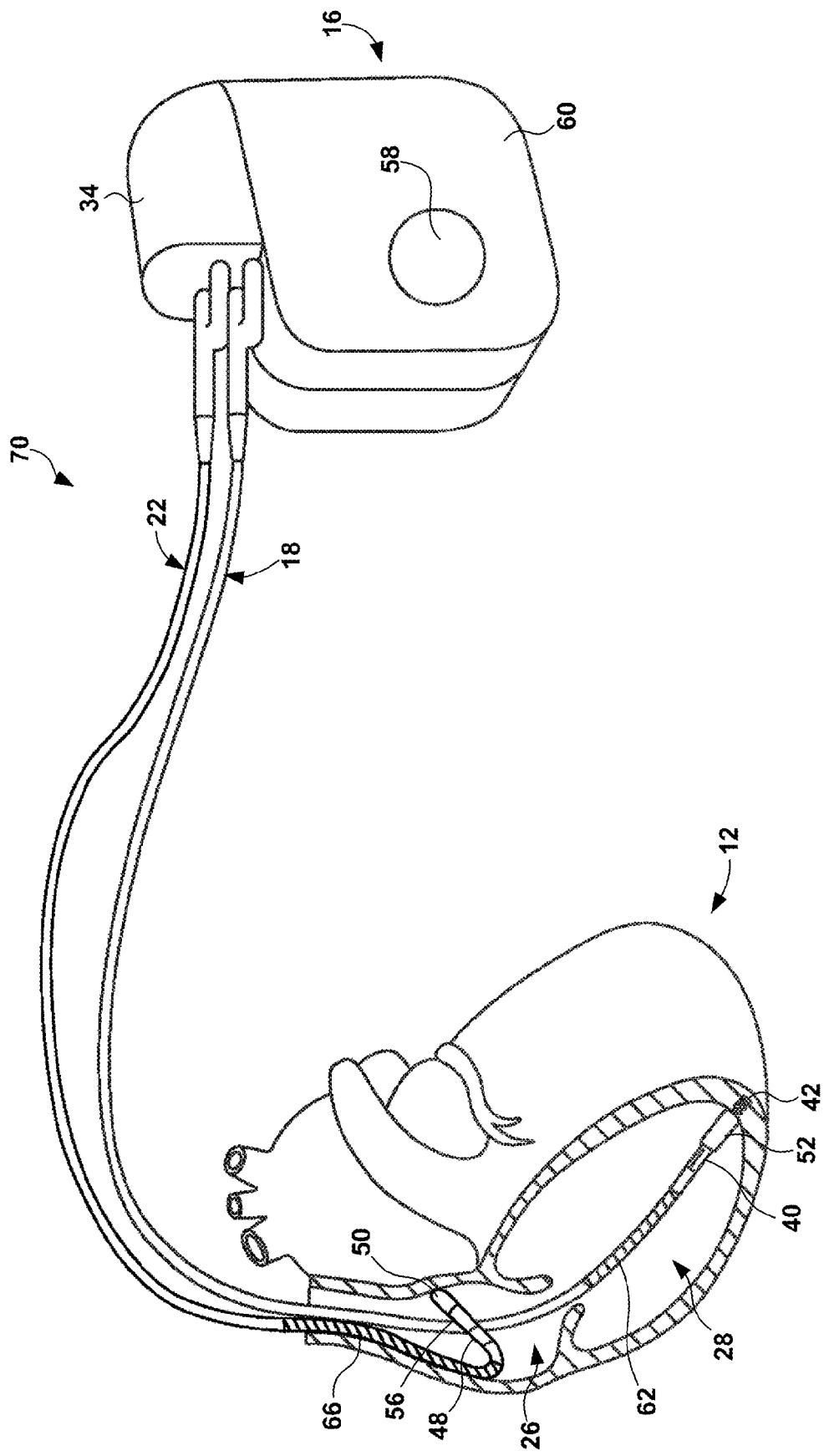
FIG. 3 is a conceptual diagram illustrating another example therapy system.

FIG. 3 is a conceptual diagram illustrating another example of therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for providing defibrillation, cardioversion and pacing pulses to heart 12, and for performing any of the techniques for distinguishing ventricular and supraventricular tachycardias described herein.

Figure 4:
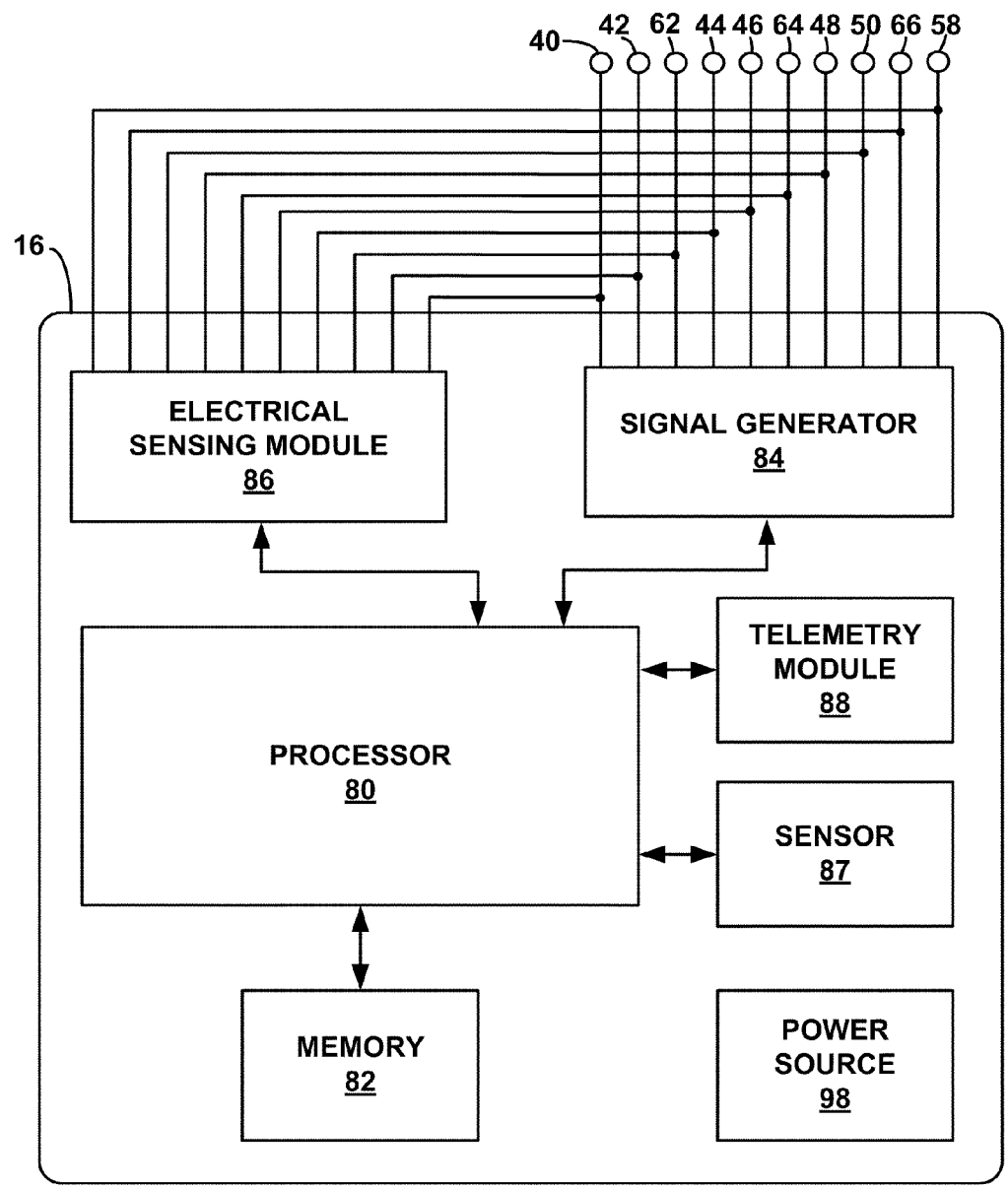
FIG. 4 is a functional block diagram illustrating an example configuration of an IMD.

FIG. 4 is a functional block diagram illustrating one example configuration of IMD 16. In the example illustrated by FIG. 4, IMD 16 includes a processor 80, memory 82, signal generator 84, electrical sensing module 86, sensor 87, telemetry module 88, and power source 98. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls sensing module 86 to sense and signal generator 84 to deliver stimulation therapy to heart 12 according to operational parameters, which may be stored in memory 82.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing and, optionally, cardioversion and/or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple a signal to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the cardiac activity. In some examples, processor 80 may select the electrodes that function as sense electrodes, or the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in a respective chamber of heart 12, and may be configured to detect either R-waves or P-waves, which may be indicative of atrial and ventricular depolarization, respectively. In some examples, electrical sensing module 86 or processor 80 may include an analog-to-digital converter for digitizing the signal received from a sensing channel for electrogram signal processing by processor 80. In response to the signals from processor 80, the switch module within electrical sensing module 86 may couple the outputs from the selected electrodes to one of the detection channels or the analog-to-digital converter.

Escape interval counters maintained by processor 80 may be reset upon sensing of R-waves and P-waves with respective detection channels of electrical sensing module 86. Processor 80 may reset the escape interval counters upon detection of an intrinsic depolarization in a chamber. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as an atrial or ventricular fibrillation or tachycardia. Processor 80 may also use the count in the interval counters to more generally monitor heart rate and/or classify a tachyarrhythmia event based on the ratio of atrial complexes to ventricular complexes. As one example, processor 80 may classify a tachycardia as a 1:1 tachycardia, i.e., exhibiting one atrial complex per one ventricular complex.

In some examples, processor 80 may control signal generator 84 to deliver a pacing pulse to a chamber upon expiration of an escape interval. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one or more of the chambers of heart 12. The escape interval counters may be reset upon delivery of a pacing pulse.

Processor 80 may also use R-wave and/or P-wave detection channels of electrical sensing module 86 to measure durations of R-R intervals, P-P intervals, P-R intervals and R-P intervals for purposes of monitoring heart rate variability (HRV). HRV may provide an indication of autonomic tone. Low HRV indicates sympathetic predominance, while high HRV indicates parasympathetic predominance. If processor 80 detects a tachycardia, processor 80 may examine heart rate and HRV to distinguish between SVT and VT. As described in further detail below, SVT and VT may exhibit different heart rate and HRV patterns. In some examples, processor 80 monitors heart rate and HRV on heartbeat-by-heartbeat basis to detect acute changes. Memory 82 may store values indicative of heart rate and HRV.

In general, processor 80 may assess HRV by analyzing any electrical signal sensed by electrical sensing module 86. For example, processor 80 may analyze a sensed electrogram signal or a signal derived from a sensed electrogram signal in the time and/or frequency domain. As one example, processor 80 may calculate a ratio of a high frequency component of a frequency spectrum of HRV to a low frequency component of the frequency spectrum of HRV to assess the autonomic tone of a patient.

Processor 80 may also perform electrogram signal processing to monitor atrioventricular (AV), i.e., antegrade, and ventriculo-atrial (VA), i.e., retrograde, conduction. For example, processor 80 may periodically determine whether AV and VA conduction is present, e.g., regardless of whether a tachycardia rhythm is currently detected or specifically when a tachycardia rhythm is not detected. If processor 80 detects a tachycardia, e.g., a 1:1 tachycardia that exhibits one atrial complex per one ventricular complex, processor 80 may refer to a previous examination of AV and VA conduction to distinguish between SVT and VT. If VA conduction is not present on a consistent basis, processor 80 may classify the tachycardia as SVT, since VT may be associated with VA conduction. Likewise, if AV conduction is not present on a consistent basis, processor 80 may classify the tachycardia as VT, since SVT may be associated with AV conduction.

IMD 16 may also include one or more sensors 87 separate from electrodes 40, 42, 44, 46, 48, 50, 58, 62, 64 and 66. Via a signal generated by sensor 87, processor 80 may monitor one or more physiological parameters indicative of cardiac contraction. Examples of sensors 87 that may generate a signal indicative of cardiac contraction include an intracardiac or intravascular pressure sensor, an accelerometer or other sensor capable of detecting heart or blood sounds, vibrations, or motion, an optical or ultrasonic sensor capable or detecting changes in flow associated with cardiac contractions, or an optical sensor capable of detecting oxygen saturation changes associated with cardiac contractions. Processor 80 may detect cardiac contractions based on signals from one or more sensors 87, and determine HRV based on the intervals between contractions in a manner similar to determining HRV based on P-P or R-R intervals.

In some examples, memory 82 stores one or more threshold values that processor 80 references to detect tachycardia rhythms. For example, memory 82 may store a value for a lower threshold limit of a tachycardia zone. Processor 80 may compare a sensed heart rate of patient 14 to the lower threshold limit and detect a tachycardia rhythm if the sensed heart rate exceeds the lower threshold limit stored in memory 82. In some examples, memory 82 may store more than one threshold, and thereby define a plurality of tachycardia zones.

In some examples, processor 80 may record, e.g., and store in memory 82, how often the sensed heart rate is proximate to the lower threshold limit, e.g., based on the number of times and/or duration of time the sensed heart rate is proximate to the lower threshold limit. For example, processor 80 may monitor when the sensed heart rate falls within a certain percentage of the lower threshold limit, e.g., plus and/or minus ten percent of the lower limit. Processor 80 may monitor one or both of when the sensed heart rate is proximate to and above the lower limit or proximate to and below the lower threshold limit.

When the sensed heart rate is proximate to the lower limit, processor 80 may confirm that the heart rate is exhibiting sinus tachycardia. For example, processor 80 may apply any suitable SVT and VT discrimination technique to classify the heart rate. Processor 80 may detect sinus tachycardia if the discrimination technique yields SVT and the heart rate is proximate to the lower threshold limit. Confirming that sinus tachycardia is present may prevent other tachycardia rhythms, e.g., VT, from going undetected.

If the sensed heart rate falls proximate to the lower threshold limit and is classified as sinus tachycardia a specified number of times, for a specified duration, or for a specified number of times of at least a specified duration, processor 80 may increase the lower threshold limit of the tachycardia zone, e.g., within certain programming limits. For example, processor 80 may increase the lower threshold limit by a specified increment or percentage. In examples in which memory 82 stores a plurality of thresholds that define a plurality of zones, processor 80 may increase only the lower threshold limit, or may similarly increase some or all of the thresholds.

Processor 80 may increase the lower threshold limit automatically or request confirmation from a user, e.g., via telemetry module 88. In examples in which processor 80 automatically adjusts the lower threshold limit, telemetry module 88 may send a notification to a user, e.g., patient or clinician, via telemetry module 88 in response to the automatic adjustment. Increasing the lower threshold limit in this manner may prevent processor 80 from repeatedly classifying a fast sinus rhythm as a tachycardia rhythm. Processor 80 may also decrease the lower threshold limit, e.g., back toward a previous value, if the heart rate of patient 14 becomes slower, as determined by processor 80.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 receive downlinked data from programmer 24 via an address/data bus. In some examples, telemetry module 88 may provide received data to processor 80 via a multiplexer.

In some examples, processor 80 may transmit indications of detected tachycardia rhythms to programmer 24 via telemetry module 88. For example, processor 80 may store information each time a tachycardia rhythm is detected along with an indication of whether the tachycardia was classified as SVT or VT within memory 82. Upon interrogation by programmer 24, processor 80 may control telemetry module 88 to transmit the information regarding detected tachycardia events stored in memory 82. As another example, telemetry module 88 may transmit raw signals, e.g., electrogram signals, to programmer 24. Programmer 24 may, in turn, perform signal processing to detect and classify tachycardia events, e.g., as SVT or VT. In examples in which processor 80 detects tachycardia rhythms and classifies the detected rhythms as SVT or VT, telemetry module 88 may transmit a notification, e.g., to programmer 24, when a particular event, such as VT, is identified.

In some examples, processor 80 may automatically select the therapy delivered by signal generator 82 based on a particular classification of a detected tachycardia event. For example, processor 80 may control signal generator 82 to deliver anti-tachycardia pacing to patient 14 if a detected tachycardia is classified as VT.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis. In other examples, power source 90 may include a supercapacitor.

Figure 5:
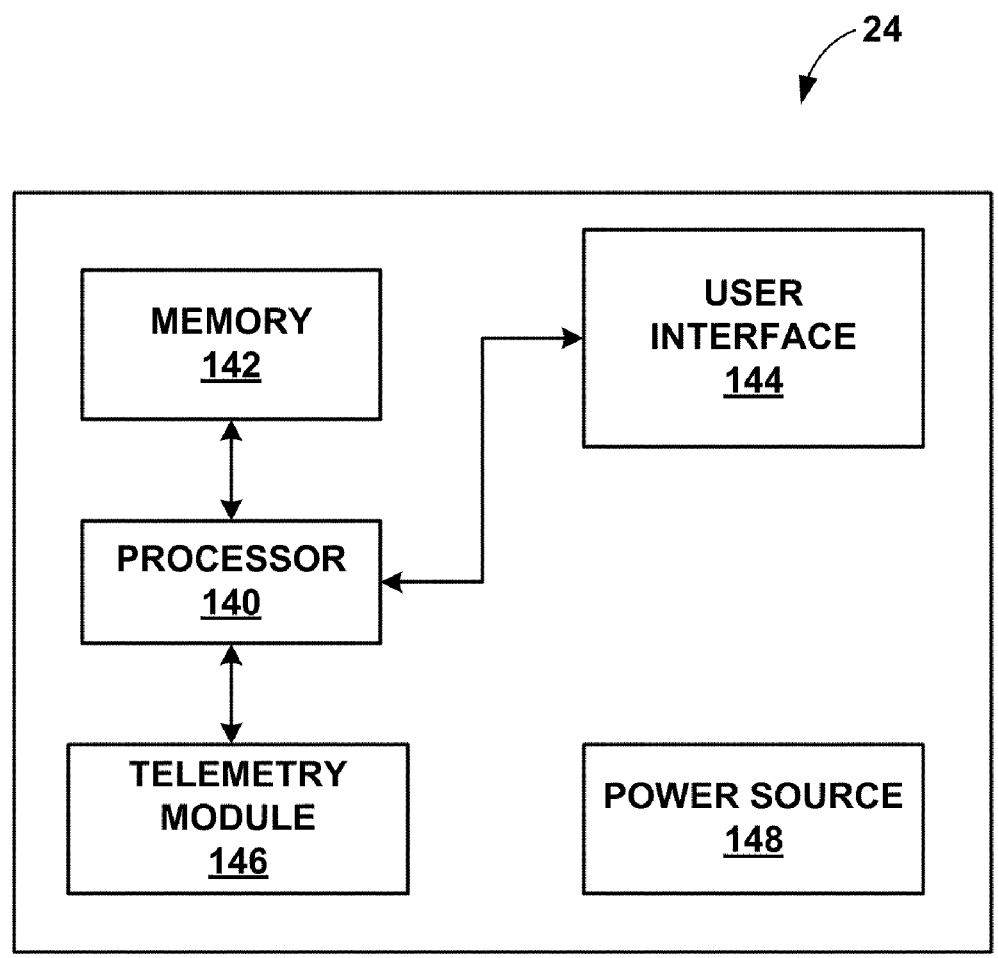
FIG. 5 is block diagram of an example external programmer that facilitates user communication with the IMD.

FIG. 5 is block diagram of an example programmer 24. As shown in FIG. 5, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of operational parameters), generate new therapy programs, or modify therapy programs for IMD 16. The clinician may interact with programmer 24 via user interface 144 which may include display to present a graphical user interface to a user, and a keypad or another mechanism for receiving input from a user.

Processor 14 can take the form one or more microprocessors, DSPs, ASICs, FPGAs, programmable logic circuitry, or the like, and the functions attributed to processor 102 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 142 may be similar to telemetry module 88 of IMD 16 (FIG. 4).

Telemetry module 142 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 may be configured to provide some or all of the functionality ascribed to processor 80 of IMD 16 herein. For example, processor 140 may receive indications of cardiac depolarizations or contractions, a signal from one or more sensors 87, or information regarding autonomic tone or heart rate variability from IMD 16 via telemetry module 146. In some examples, processor 140 may detect a tachycardia, classify a tachycardia as SVT or VT, provide a notification, or initiate a therapy change, as described herein with respect to IMD 16 and processor 80.

Figure 6:
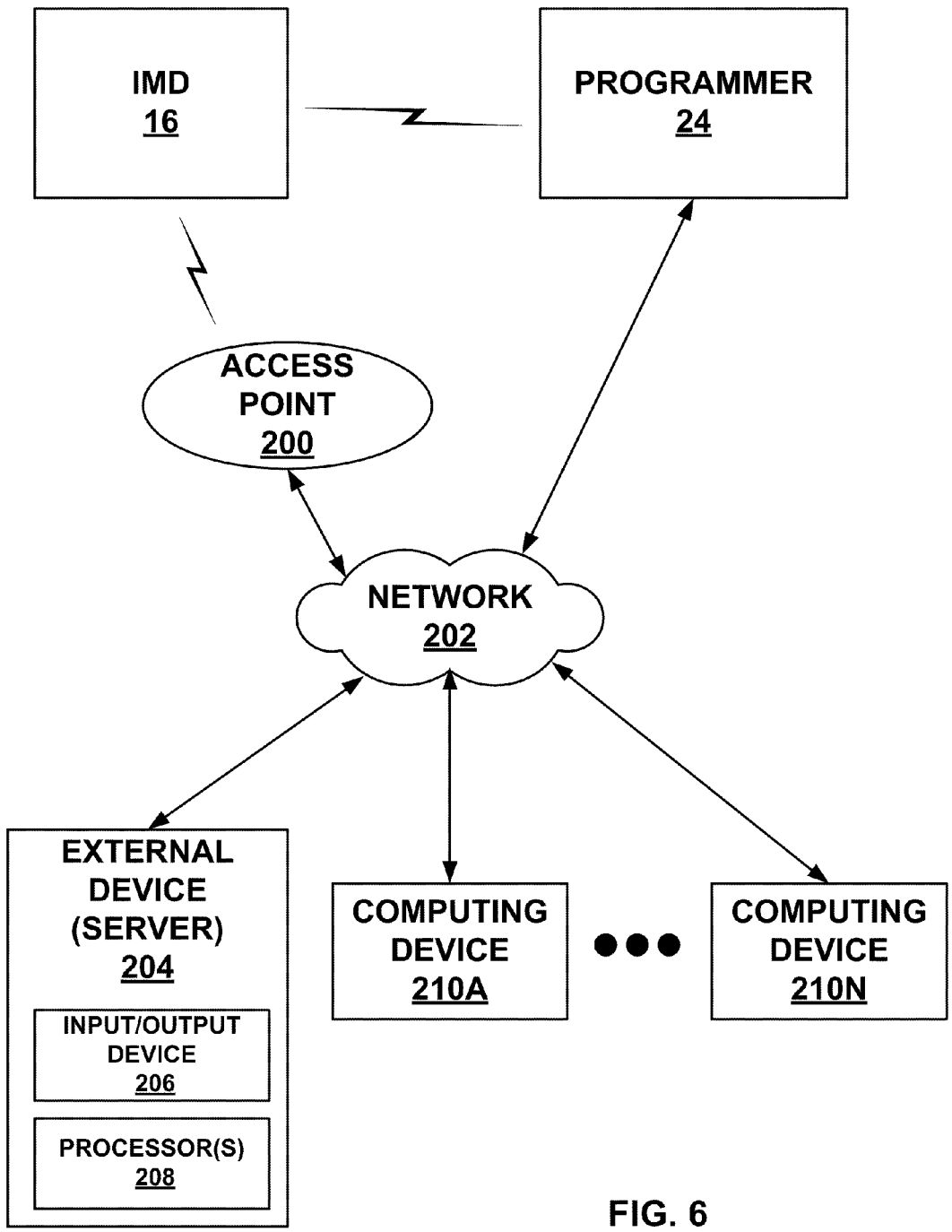
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 186 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 6 may be implemented, in some aspects, with general network technology and functionality similar to that provided by the Medtronic CareLink® Network developed by Medtronic, Inc., of Minneapolis, Minn.

In some examples, processor 208 of server 204 may be configured to provide some or all of the functionality ascribed to processor 80 of IMD 16 herein. For example, processor 206 may receive indications of cardiac depolarizations or contractions, a signal from one or more sensors 87, or information regarding autonomic tone or heart rate variability from IMD 16 via access point 200 or programmer 24 and network 202. Processor 206 may detect a tachycardia, classify a tachycardia as SVT or VT, provide a notification, or initiate a therapy change via network 202 and programmer 24 or access point 200. Processor 208 may provide a notification by sending a notification to one or more computing devices 210 via network 202. In some examples, server 204 relays a notification or indication of therapy change provided by one or more of IMD 16 or programmer 24 to one or more of computing devices 210 via network 202.

FIGS. 7A, 7B, 8-10, and 12 are flow diagrams of example methods of discriminating SVT from VT. The functionality described with respect to FIGS. 7A, 7B, 8-10, and 12 as being provided by a particular processor or device may, in other examples, be provided by any one or more of the processors or devices described herein.

Figure 7A:
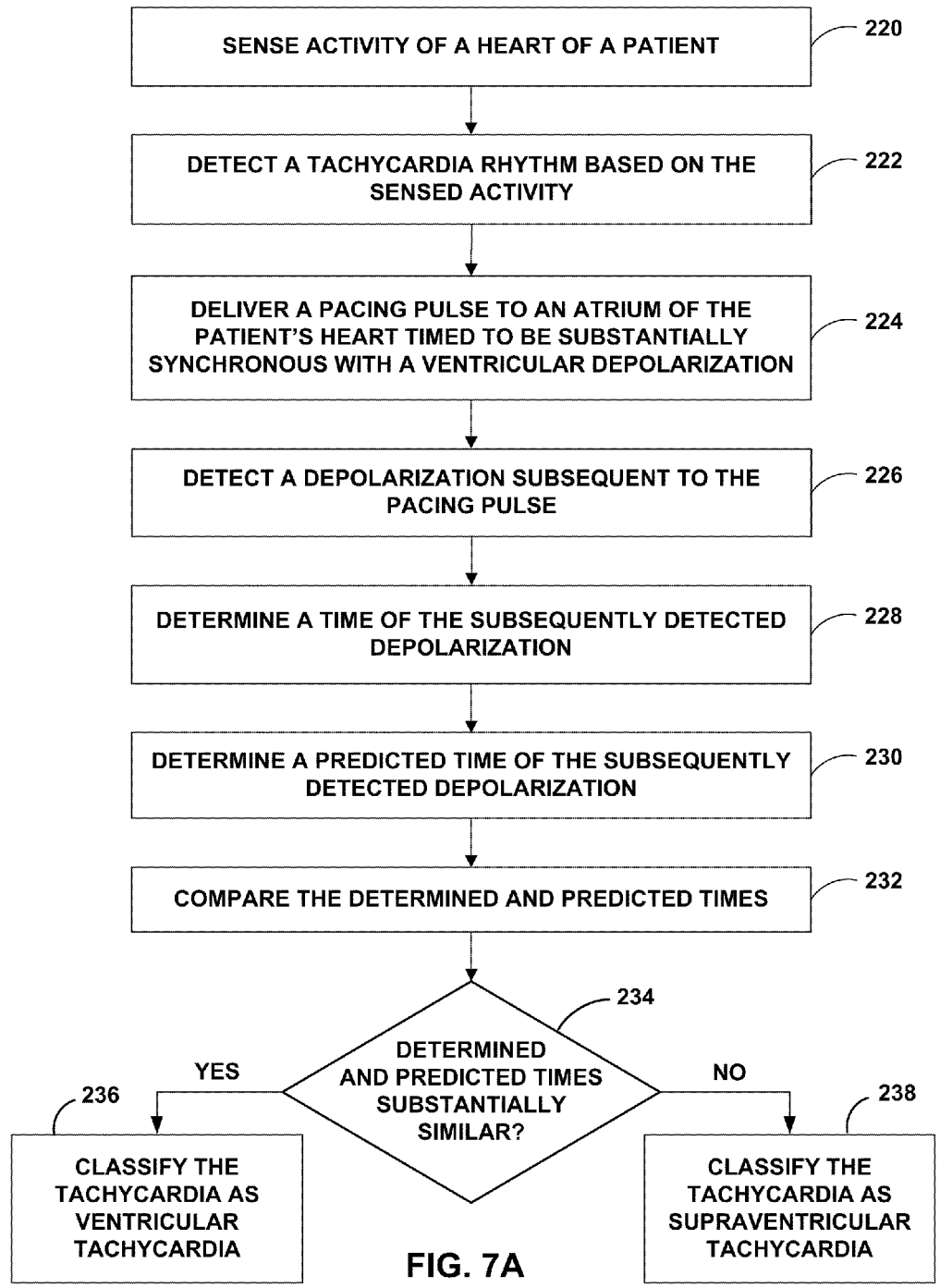
FIGS. 7A, 7B, 8-10 are flow diagrams of example methods of discriminating supraventricular tachycardia (SVT) from ventricular tachycardia (VT).

FIG. 7A is a flow diagram of an example method of discriminating SVT from VT based on a response to delivery of stimulation to an atrium. IMD 16, e.g., via electrical sensing module 86 and/or sensors 87, senses activity of heart 12 of patient 14 (220). Processor 80 of IMD 16 may detect a tachycardia rhythm based on the sensed activity (222). Memory 82 may store one or more threshold values that processor 80 may access to detect the tachycardia rhythm. In some examples, processor 80 also determines whether the tachycardia rhythm exhibits one atrial complex per one ventricular complex, i.e., as in 1:1 tachycardia.

Signal generator 84, under the control of processor 80, delivers a pacing pulse to an atrium, e.g., right atrium 26 and/or left atrium 36, of heart 12 (224). The pacing pulse may be timed to be substantially synchronous with a ventricular contraction. For example, processor 80 may predict the timing of the ventricular depolarization based on sensed cardiac activity preceding the ventricular depolarization, e.g., based on the timing of previously sensed ventricular depolarizations, and deliver the pacing pulse at the predicted time of the ventricular depolarization. As another example, processor 80 may detect the ventricular depolarization based on sensed cardiac activity and deliver the pacing pulse in response to the detected ventricular depolarization. In this manner, signal generator 84 may deliver the pacing pulse while the ventricular depolarization is underway or just after the detected ventricular depolarization and prior to a subsequent atrial depolarization.

Processor 80 detects a depolarization subsequent to the pacing pulse (226) and determine a time of the subsequently detected depolarization (228). Processor 80 also determines a predicted time of the subsequently detected depolarization, e.g., based on the pattern and timing of depolarizations sensed prior to delivery of the pacing pulse (230) and compares the determined and predicted times (232).

In the case of VT, the antegradely conducting atrial depolarization traveling from the atrium to the ventricle induced by the pacing pulse may collide with the retrogradely conducting depolarization traveling from the ventricle to the atrium corresponding to the VT, e.g., in the atrioventricular (AV) node or His-purkinje system. Thus, the propagation of the atrial depolarization induced by the pacing pulse may be prevented by the opposing retrogradely conducting depolarization corresponding to the VT. Therefore, the atrial depolarization induced by the pacing pulse may not perturb the VT. The next atrial and ventricular depolarizations may occur at predicted times, e.g., consistent with the timing of detected atrial and ventricular depolarizations preceding the pacing pulse.

In the case of SVT, e.g., atrial tachycardia or sinus tachycardia, the pacing pulse may reset the tachycardia and the next atrial and ventricular depolarizations may not occur at the predicted times, e.g., may be inconsistent with the timing of detected atrial and ventricular depolarizations preceding the pacing pulse. For example, the subsequent atrial and ventricular depolarizations may be delayed relative to their predicted times.

Processor 80 determines if the actual, determined time of the subsequently detected depolarization is substantially similar to the predicted time (234). For example, processor 80 may determine whether the determined time is within a threshold value of the predicted time. If the determined and predicted times are substantially similar, processor 80 may classify the tachycardia as VT (236). If the determined and predicted times are not substantially similar, e.g., the determined time is a threshold amount later than the predicted time, processor 80 may classify the tachycardia as SVT (238). The determined and predicted times may be intervals from a common origin, such as the delivery of the atrial stimulation.

Figure 7B:
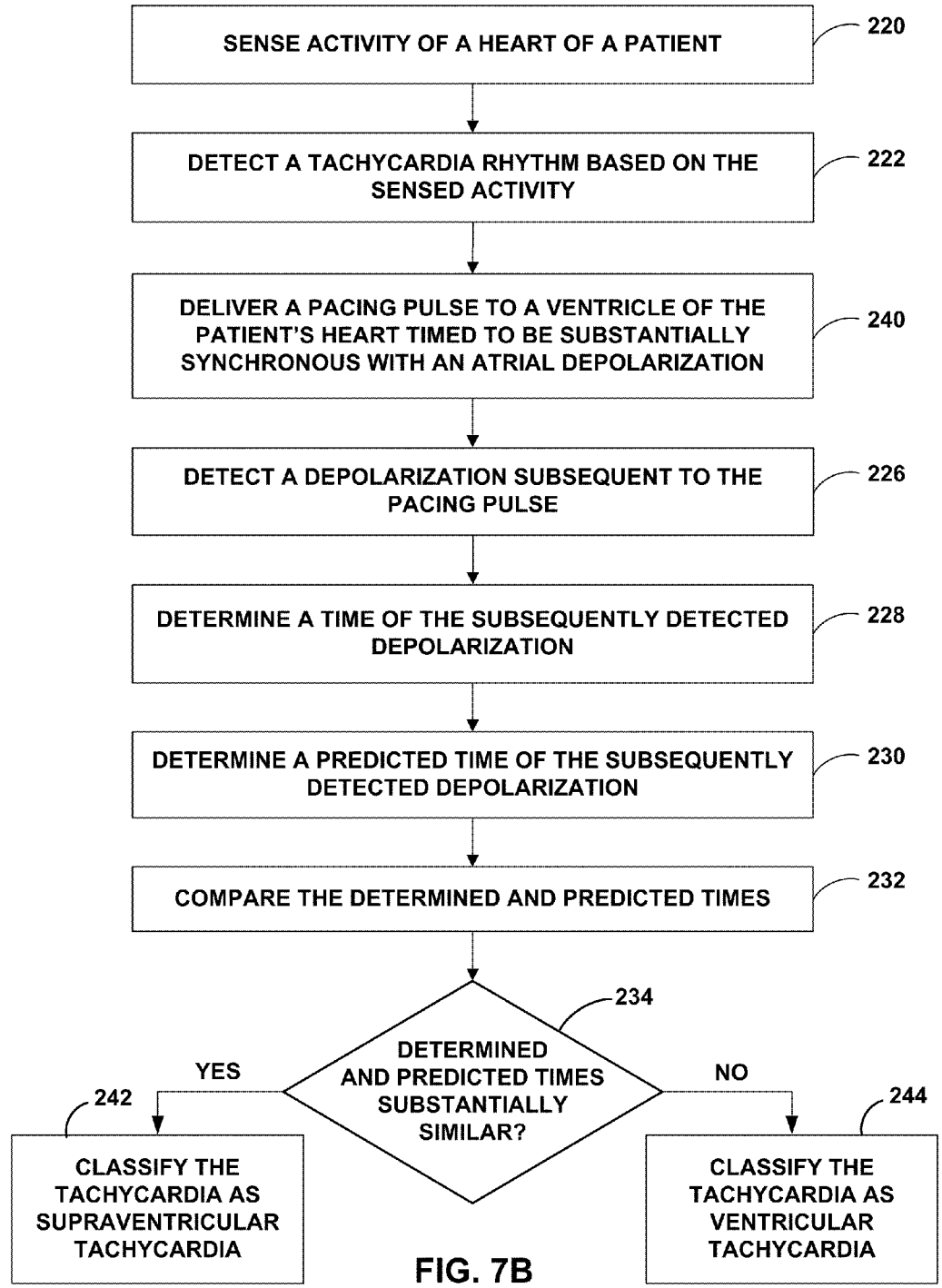

FIG. 7B is a flow diagram of another example method of discriminating SVT from VT based on a response to delivery of stimulation to a ventricle. FIG. 7B is substantially similar to FIG. 7A but includes an alternative method of delivering a pacing pulse to heart 12 of patient 14. As described with respect to FIG. 7A, IMD 16 senses activity of heart 12 of patient 14 (220), and processor 80 of IMD 16 detects a tachycardia rhythm based on the sensed activity (222).

Signal generator 84, under the control of processor 80 delivers a pacing pulse to a ventricle, e.g., right ventricle 28 and/or left ventricle 32, of heart 12 (240). The pacing pulse may be timed to be substantially synchronous with an atrial contraction. For example, processor 80 may predict the timing of the atrial depolarization based on sensed cardiac activity preceding the atrial depolarization, e.g., based on the timing of previously sensed atrial depolarizations, and deliver the pacing pulse at the predicted time of the atrial depolarization. As another example, processor 80 may detect the atrial depolarization based on sensed cardiac activity and deliver the pacing pulse in response to the detected atrial depolarization. In this manner, signal generator 84 may deliver the pacing pulse while the atrial depolarization is underway or just after the detected atrial depolarization and prior to a subsequent ventricular depolarization.

As described with respect to FIG. 7A, processor 80 detects a depolarization subsequent to the pacing pulse (226) and determines a time of the subsequently detected depolarization (228). Processor 80 may also determine a predicted time of the subsequently detected depolarization, e.g., based on the pattern and timing of depolarizations sensed prior to delivery of the pacing pulse (230) and compare the determined and predicted times (232). Processor 80 may determine if the actual, determined time of the subsequently detected depolarization is substantially similar to the predicted time (234).

In the case of SVT, the antegradely conducting spontaneous depolarization traveling from the atrium to the ventricle may collide with the retrogradely conducting depolarization traveling from the ventricle to the atrium induced by the pacing pulse, e.g., in the AV node or His-purkinje system, and the next atrial and ventricular depolarizations may occur at predicted times, e.g., consistent with the timing of detected atrial and ventricular depolarizations preceding the pacing pulse. In the case of VT, the pacing pulse may reset the tachycardia and the next atrial and ventricular depolarizations may not occur at the predicted times, e.g., may be inconsistent with the timing of detected atrial and ventricular depolarizations preceding the pacing pulse. Thus, processor 80 may classify the tachycardia as SVT if the determined and predicted times are substantially similar (242) or VT if the determined and predicted times are not substantially similar (244).

Figure 8:
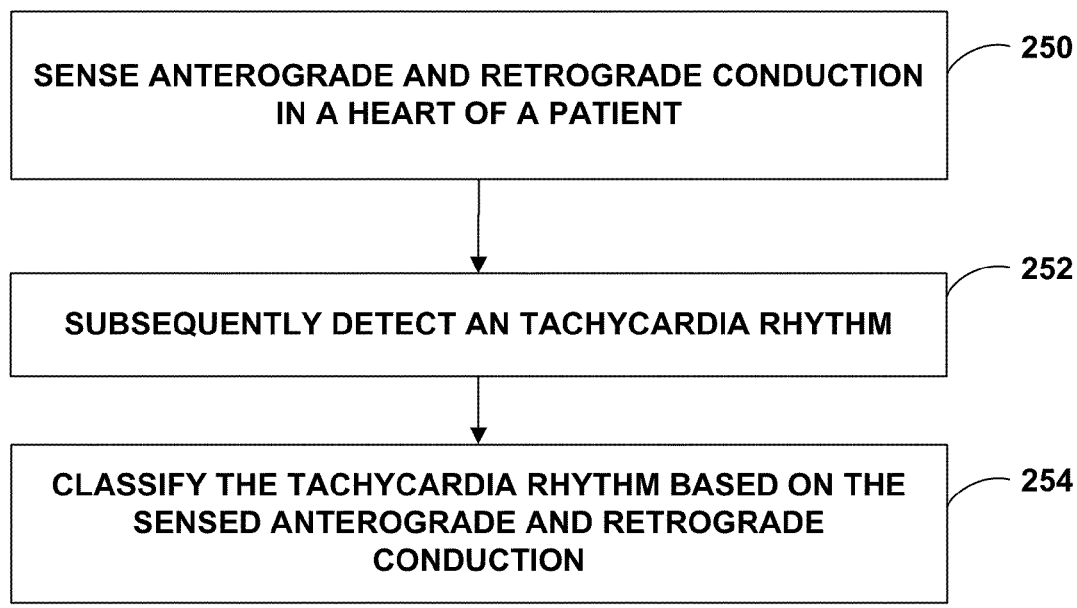

FIG. 8 is a flow diagram of another example method of discriminating SVT from VT. Processor 80 may sense antegrade and retrograde conduction heart 12 of patient 14, e.g., via electrical sensing module 86 or sensors 87 (250). In some examples, processor 80 periodically determines whether AV and VA conduction is present, e.g., regardless of whether a tachycardia rhythm is currently detected or specifically when a tachycardia rhythm is not detected. In various examples, processor 80 determines the presence of AV and VA conduction by monitoring the relative timing of atrial and ventricular depolarizations or contractions for evidence of AV and VA conduction. In some examples, processor 80 controls signal generator 84 to deliver stimulation, e.g., a pacing pulse, to one of the atria and the ventricles, and monitors for a response in the other of the atria and the ventricles.

Processor 80 may subsequently detect a tachycardia rhythm in heart 12 of patient 14 (252). For example, processor 80 may compare a detected heart rate of patient 14 to one or more tachycardia thresholds stored and memory 82 and detect the tachycardia rhythm based on the comparison. In some examples, processor 80 may also determine if the detected tachycardia rhythm exhibits one atrial complex per one ventricular complex, i.e., comprises 1:1 tachycardia.

Processor 80 may classify the tachycardia rhythm as SVT or VT based on the sensed antegrade and retrograde conduction (254). For example, processor 80 may classify the tachycardia rhythm as SVT if retrograde conduction was not consistently sensed prior to the detected tachycardia, since VT may be associated with VA conduction. Likewise, if antegrade conduction was not consistently sensed prior to the detected tachycardia, processor 80 may classify the tachycardia as VT, since SVT may be associated with AV conduction.

Figure 9:
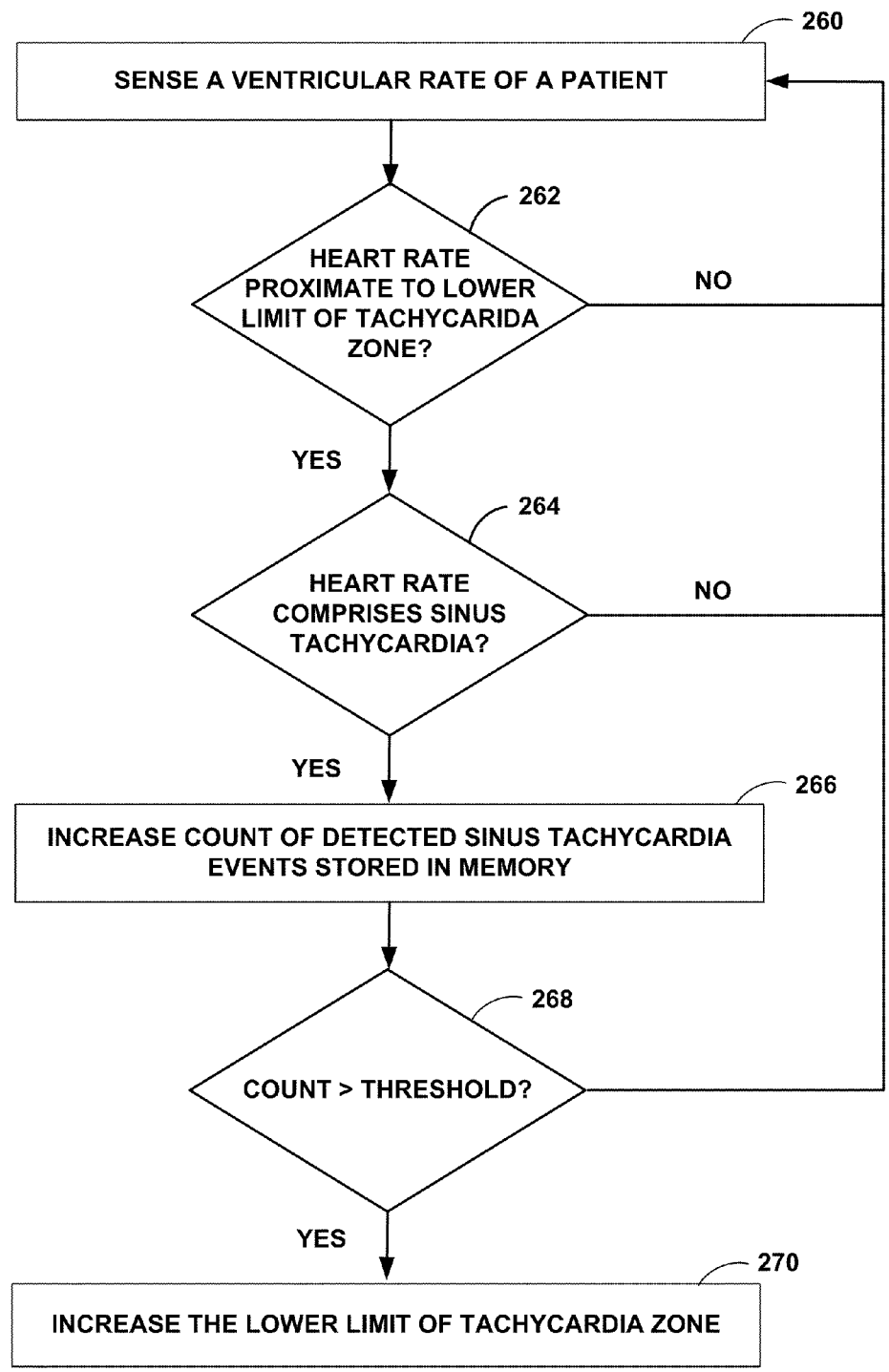

FIG. 9 is a flow diagram of another example method of discriminating SVT from VT that includes modification of a lower threshold limit of a VT zone. According to the example method of FIG. 9, processor 80 senses a ventricular rate of heart 12 of patient 14, e.g., via electrical sensing module 86 and/or sensors 87 (260) and periodically determines whether the sensed heart rate is proximate to a lower threshold limit of a tachycardia zone (262). For example, processor 80 may monitor when the sensed ventricular rate falls within a certain percentage of the lower threshold limit, e.g., plus and/or minus ten percent of the lower limit. Processor 80 may monitor one or both of when the sensed ventricular rate is proximate to and above the lower limit or proximate to and below the lower threshold limit. If the sensed ventricular rate is not proximate to the lower threshold limit, processor 80 continues sensing the heart rate of patient 14 (260).

If the sensed ventricular rate is proximate to the lower threshold limit of the tachycardia zone, processor 80 determines whether the heart rate comprises sinus tachycardia (264). For example, processor 80 may apply any suitable discrimination technique, including those described herein, to classify the heart rate. In some examples, processor 80 may detect sinus tachycardia if the discrimination technique yields SVT and the heart rate is proximate to the lower threshold limit. Confirming that sinus tachycardia is present may prevent other tachycardia rhythms, e.g., VT, from going undetected. If the tachycardia rhythm is not sinus tachycardia, processor 80 may continue monitoring the heart rate of patient 14 (260).

If the tachycardia rhythm is sinus tachycardia, processor 80 may increase the count of sinus tachycardia events detected proximate to the lower threshold limit of the tachycardia zone (266) and determine whether the count exceeds a threshold value, e.g., stored in memory 82 (268). The threshold value may represent a number of times a sinus tachycardia event proximate to the lower threshold limit of the tachycardia zone must be detected before processor 80 takes a specified action. In some examples, in order to be counted, a sinus tachycardia event proximate to the lower threshold must persist for a threshold duration, which may be a time or number of ventricular depolarizations. In other examples, the threshold may be another parameter indicative of the burden of sinus tachycardia events proximate to the lower threshold limit of the tachycardia zone, such as a duration of one event, a sum of durations of a plurality of such events, a sum of durations of the previous X events, or a sum of the durations of events over a predetermined time period. In other examples, processor 80 may respond in the manner discussed below to each occurrence of a sinus tachycardia event proximate to the lower threshold limit without requiring a burden threshold to be satisfied. In the example of FIG. 9, if the count does not exceed the threshold value, processor 80 continues monitoring the ventricular rate of patient 14 (260).

If the count does exceed the threshold value, processor 80 increases the lower threshold limit of the tachycardia zone, e.g., within certain programming limits stored in memory 82 (270). For example, processor 80 may increase the lower threshold limit by a specified increment or percentage. Processor 80 may increase the lower threshold limit automatically or request confirmation from a user, e.g., via telemetry module 88. In examples in which processor 80 automatically adjusts the lower threshold limit, telemetry module 88 may send a notification to a user, e.g., patient or clinician, via telemetry module 88 in response to the automatic adjustment. Increasing the lower threshold limit in this manner may prevent processor 80 from repeatedly classifying a fast sinus rhythm as a tachycardia rhythm. Processor 80 may also decrease the lower threshold limit, e.g., back toward a previous value, if the heart rate of patient 14 becomes slower, as determined by processor 80.

Figure 10:
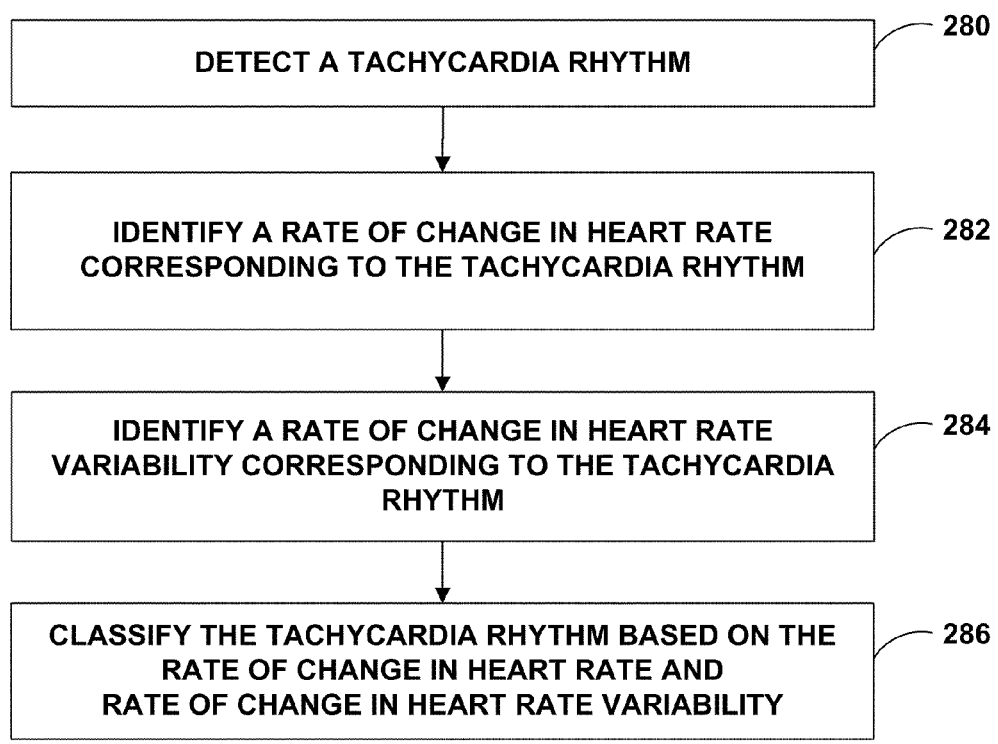

FIG. 10 is a flow diagram illustrating another example method of distinguishing SVT from VT. Processor 80 detects a tachycardia rhythm (280). As described previously, processor 80 may monitor the heart rate of patient 24, e.g., via electrical sensing module 86 and/or sensors 87 and compare the detected heart rate to one or more tachycardia thresholds stored in memory 82. As described previously, monitoring the heart rate may include monitoring one or both of a ventricular rate and an atrial rate.

Processor 80 identifies a rate of change in heart rate corresponding to the tachycardia rhythm (282) and a rate of change in heart rate variability (HRV) corresponding to the tachycardia rhythm (284). For example, processor 80 may use R-wave and/or P-wave detection channels of electrical sensing module 86 to measure durations of R-R intervals, P-P intervals, P-R intervals and R-P intervals for purposes of monitoring HRV. In some examples, processor 80 monitors heart rate and HRV on heartbeat-by-heartbeat basis to detect acute changes. Memory 82 may store values indicative of heart rate and HRV. Upon detection of a tachycardia rhythm (280), processor 80 may associate heart rate and HRV as well as temporal changes in these parameters that occur prior to and during the detected tachycardia with the detected tachycardia.

Figure 11A:
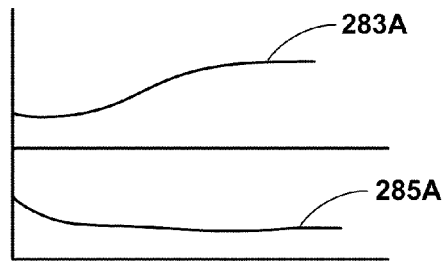
FIGS. 11A-11G are conceptual diagrams illustrating some example heart rate and heart rate variability patterns that different types of tachycardias may exhibit.
Figure 11B:
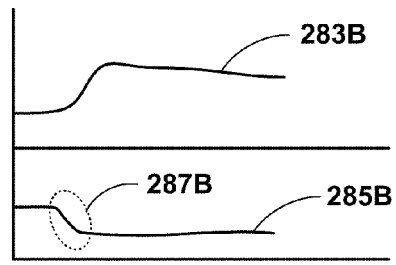
Figure 11C:
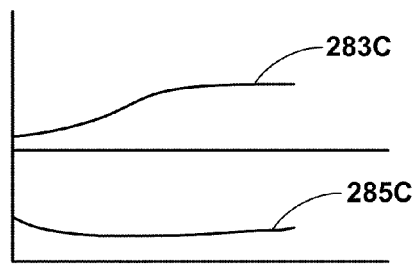

HRV may provide an indication of autonomic tone. Low HRV indicates sympathetic predominance, while high HRV indicates parasympathetic predominance. SVT and VT may exhibit different heart rate and HRV patterns. FIGS. 11A-11G illustrate some example heart rate and HRV patterns that different types of tachycardias may exhibit. In each of FIGS. 11A-11G, time is represented on the horizontal axis and both heart rate and HRV are represented on the vertical axis. As illustrated in FIG. 11A, sinus tachycardia, one type of SVT, may be driven by the sympathetic nervous system and be associated with decreased HRV 285A prior to and during a rise in heart rate 283A. As illustrated in FIG. 11B, reentrant atrial tachycardia, another type of SVT, may be associated with an abrupt change in HRV 285B, e.g., a rate of change in HRV that exceeds a threshold, such as illustrated during portion 287B, substantially simultaneous with a rise in heart rate 283B. Atrial tachycardia due to enhanced automaticity, which is also a type of SVT, may occur during periods of increased sympathetic tone and decreased HRV 285C and an associated rise in heart rate 283C, as illustrated in FIG. 11C.

Figure 11D:
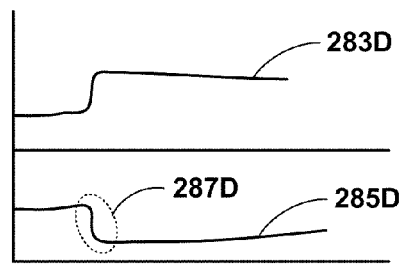

VT, and in particular fixed re-entrant VT, may be associated with an abrupt drop in HRV synchronous with onset of tachycardia. FIG. 11D illustrates an example of heart rate 283D and 285D that may be exhibited during re-entrant VT. As illustrated by portion 287D, HRV 285D may abruptly drop as heart rate 283D rises. The rate of change of HRV 285D corresponding to re-entrant VT and illustrated in FIG. 11D may be substantially greater than the rate of change of HRV 285B corresponding to re-entrant atrial tachycardia and illustrated in FIG. 11B. Additionally, the absolute change in HRV 285D corresponding to re-entrant VT illustrated in FIG. 11D may be greater than the absolute change in HRV 285B corresponding to re-entrant atrial tachycardia illustrated in FIG. 11B. This difference in the absolute change in HRV may be, at least in part, due to ventricular activation requiring passage of impulses through the AV node, which is under autonomic control, in the case of re-entrant tachycardia.

Figure 11E:
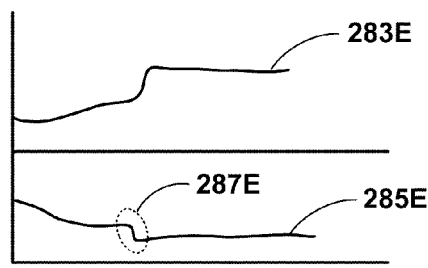

FIG. 11E illustrates an example of VT preceded by sinus tachycardia. The transition from sinus tachycardia to VT is illustrated by an abrupt decrease in HRV 285E illustrated during portion 287E and corresponding to a substantially simultaneous increase in heart rate 283E.

Figure 11F:
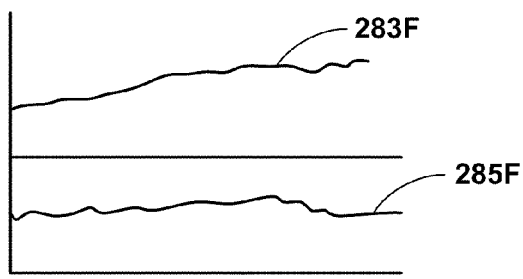
Figure 11G:
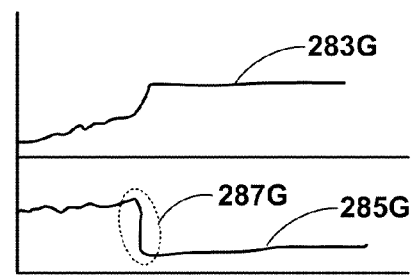

In some cases, atrial flutter may transition into VT. FIG. 11F illustrates an example of heart rate 283F and HRV 285F associated with atrial flutter. As illustrated in FIG. 11F, atrial flutter may be associated with frequent small fluctuations in both heart rate 283F and HRV 285F. FIG. 11G illustrates an example of VT preceded by atrial flutter. The transition from atrial flutter to VT illustrated by an abrupt decrease in HRV 285G illustrated during portion 287G and corresponding to a substantially simultaneous increase in heart rate 283G.

The rate of change of HRV associated with VT may be substantially greater than rates of change in HRV associated with various types of SVT, e.g., sinus and atrial tachycardia. Processor 80 may compare a rate of change in HRV detected for a tachycardia event to one or more threshold values stored in memory 82 to aid in distinguishing SVT from VT. Processor 80 may also determine whether a rate in change in HRV that exceeds the threshold value corresponds to a substantially simultaneous increase in heart rate. Returning to FIG. 10, processor 80 classifies the tachycardia rhythm as at least one of supraventricular tachycardia or ventricular tachycardia based on the heart rate and rate of change in HRV (286).

In some examples, the threshold values that processor 80 uses to discriminate between SVT and VT may be programmable. For example, the threshold values may be defined, e.g., by a clinician, before processor 80 is able to distinguish between SVT and VT. As one example, processor 80 may record heart rate and HRV data each time it detects a tachycardia episode, e.g., a heart rate that exceeds a threshold value and meets any other tachycardia detection criteria. Processor 80 may associate each detected tachycardia episode with a HRV and heart rate signature that depicts the absolute change, the rate of change, or the relative timing of change of HRV and heart rate prior to and during the tachycardia rhythm. The clinician, e.g., via programmer 24, may analyze the detected tachycardia episodes and program different threshold values for HRV and heart rate, e.g., for the change, the rate of change, or the relative timing of change of HRV and heart rate, which may be stored in memory 82 and accessed by processor 80 to automatically discriminate between different types of SVT and VT. The clinician may use the HRV and heart rate data recorded for the previously detected tachycardia episodes as a guide for programming of the threshold values.

In another example, the clinician classifies each of the detected tachycardia rhythms to as one of multiple types of SVT, e.g., sinus tachycardia, atrial tachycardia, or VT. Processor 80 may, based on instructions stored with memory 82, determine a set of threshold values which best discriminate the various types of SVT and VT based on the classifications inputted by the clinician. Processor 80 may also transmit a notification to programmer 24 via telemetry module 88 if processor 80 determines that there are no threshold values that adequately discriminate between specific types of tachycardia, e.g., between sinus tachycardia and VT. Processor 80, e.g., automatically or in response to an input received from the clinician via programmer 24, may turn the program feature for discriminating between these tachycardia types off.

If patient 14 is known to experience one or more types of SVT that may result in a rise in heart rate into the VT zone, processor 80 may discriminate between those particular types of SVT and VT rather than all types of SVT and VT. For example, a clinician may program IMD 16, e.g., via programmer 24, to discriminate between specific types of SVT and VT. For example, if patient 14 is observed to experience sinus tachycardia and VT, the clinician may instruction processor 80, e.g., via programmer 24, to disable discrimination between atrial fibrillation and VT but leave discrimination between sinus tachycardia and VT enabled. If this manner, some discrimination techniques may be enabled while others are disabled.

As another example, some discrimination techniques may be enabled or disabled based on the therapy being delivered by signal generator 84 of IMD 16. As one example, discrimination between atrial fibrillation and VT may only be enabled if IMD 16 is operating in an atrial model switched state. Processor 80 may automatically enable or disable discrimination techniques based on the operating state of IMD 16.

Figure 12:
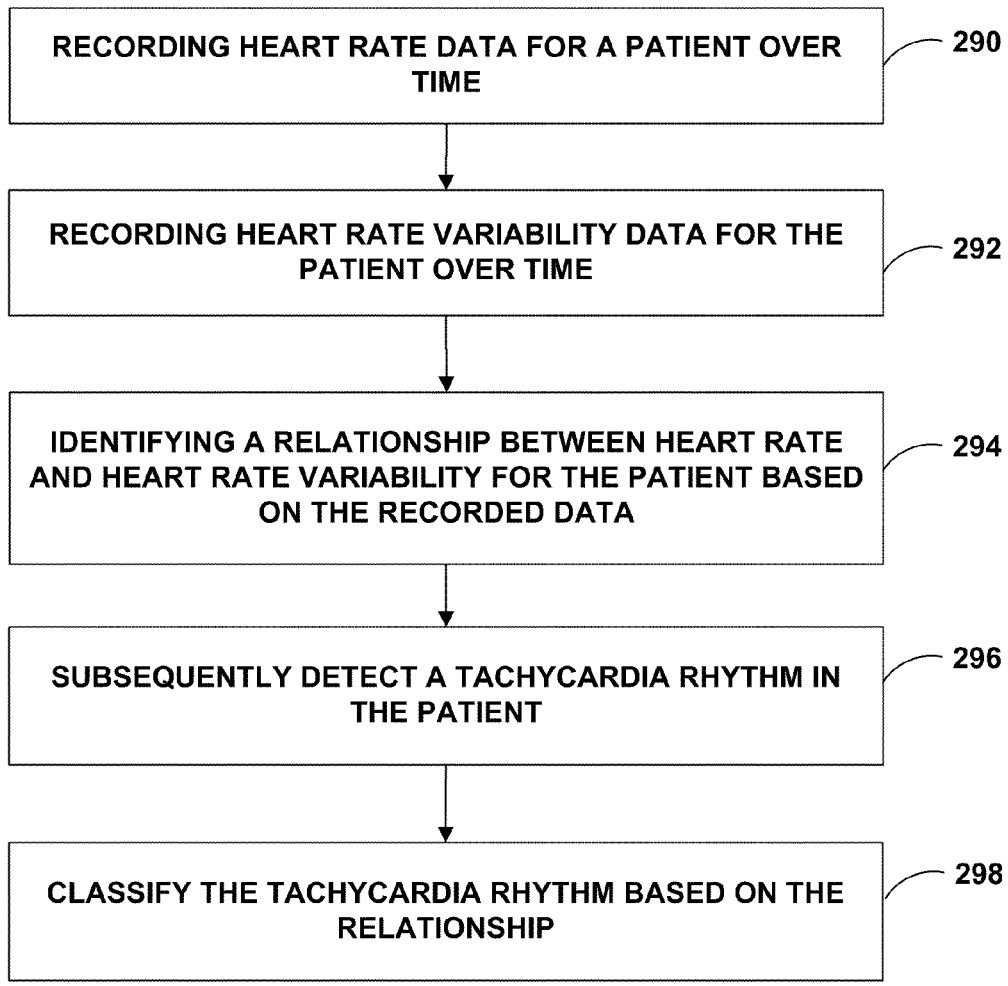
FIG. 12 is a flow diagram illustrating another example method of distinguishing SVT from VT.

FIG. 12 is a flow diagram illustrating another example method of distinguishing SVT from VT. Processor 80 records heart rate data for patient 14 over a period of time (290) and records HRV data for patient 14 over the same period of time (292). For example, processor 80 may record the heart rate of patient 14 over the patient's normal range of heart rates.

Processor 80 identifies a relationship between heart rate and HRV for patient 14 based on the recorded data (294). For example, processor 80 may determine a predictable relationship between the level of HRV and heart rate increase. The relationship may be associated with tolerance values, e.g., ranges of HRV associated with a particular heart rate of patient 14. In other examples, the heart rate and HRV data may be collected, and relationship defined, by one or more other devices. For example, an implantable or external monitor may collect the data, and the relationship may be defined by programmer 24, server 204, or a computing device 210.

Figure 13:
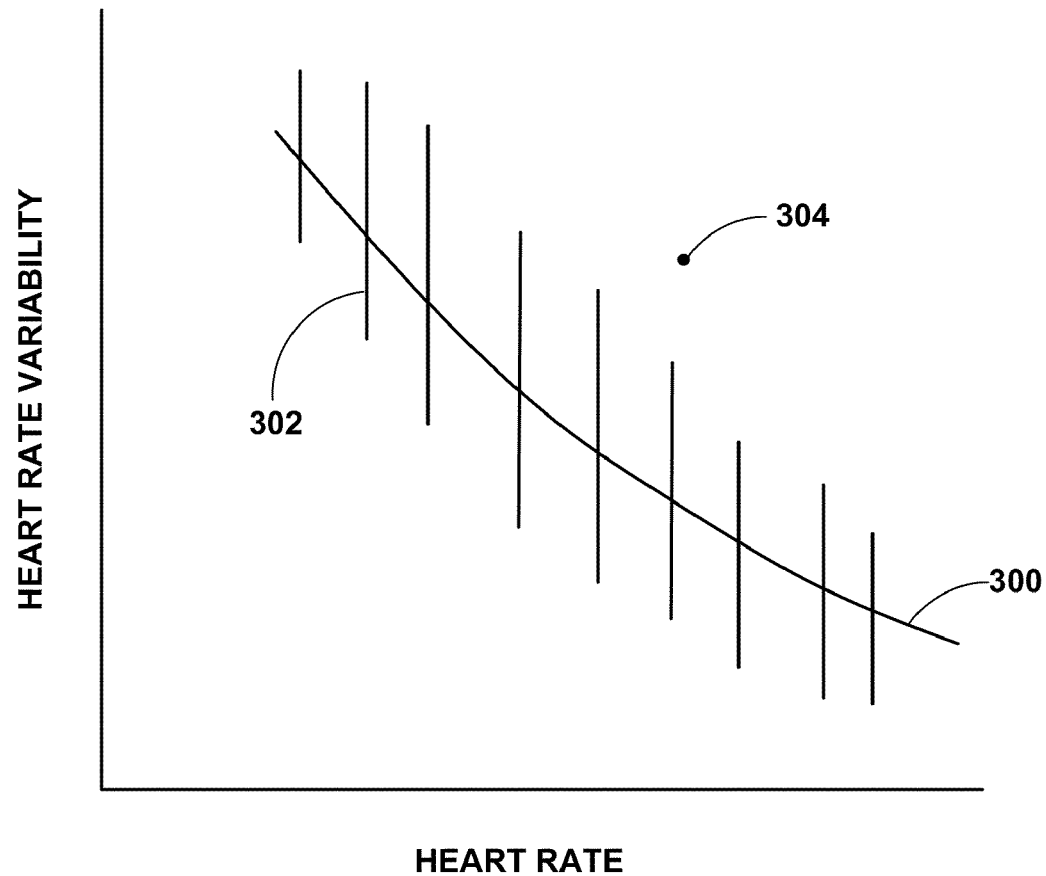
FIG. 13 is a conceptual diagram illustrating an example of a relationship between heart rate and heart rate variability that may be determined for patient 14 based on the recorded data.

FIG. 13 illustrates an example of a relationship between heart rate and HRV that may be determined for patient 14 based on the recorded data. In the example illustrated in FIG. 13, heart rate is represented on the horizontal axis and HRV is represented on the vertical axis. Relationship 300 may be defined between heart rate and HRV based on the recorded data heart rate and heart rate variability data. Relationship 300 may include tolerance values 302, which may vary based on the specific heart rate value. Tolerance values 302 define a range of "normal" or "expected" HRV values for the given heart rate value. Tolerance values may be determined by application of any statistical technique to the heart rate and HRV data collected for a patient. In one example, relationship 300 and tolerance values 302 represent a mean (or median) and standard deviation, respectively, of HRVs associated with different rates.

Returning to FIG. 12, after processor 80 identifies the relationship (294), processor 80 may subsequently detect a tachycardia rhythm in patient 14 (296) and classify the tachycardia rhythm as at least one of supraventricular tachycardia or ventricular tachycardia based on the relationship (298). For example, a heart rate in the VT zone that falls outside the extrapolated relationship, e.g., outside a tolerance of the relationship, between HRV and heart rate may indicate VT.

As one example, data point 304 illustrated in FIG. 13 may be classified as VT. Data point falls outside of the tolerance values 302 associated with relationship 300. Data point 304 illustrates an increase in heart rate without a decrease in HRV reflective of an increase in sympathetic tone that would account for the increase in heart rate. Since data point 304 does not follow relationship 300 determined for patient 14, processor 80 may classify data point 304 as VT.

In some examples, analysis of the rate, amount, or timing of HRV and HR, as described with respect to FIGS. 10 and 11A-11F, is combined with analysis of the relationship and associated tolerance between heart rate and HRV for patient 14, as described with respect to FIGS. 12 and 13, to classify a tachycardia rhythm as SVT or VT. In one example, both methods of analysis must satisfy the VT classification criteria for VT to be detected. In another example, only one method of analysis must satisfy the VT classification criteria for VT to be detected. In another example, one method of analysis is applied and the second, other method of analysis is only applied if the first method of analysis cannot conclusively classify the tachycardia rhythm as SVT or VT.

Various examples have been described. These and other examples are within the scope of the following claims.

The invention claimed is:

1. A method comprising:
   detecting a tachycardia rhythm;
   identifying a rate of change in heart rate corresponding to the tachycardia rhythm;
   identifying a rate of change in heart rate variability corresponding to the tachycardia rhythm; and
   classifying the tachycardia rhythm as at least one of supraventricular tachycardia or ventricular tachycardia based on the rate of change in heart rate and rate of change in heart rate variability, wherein classifying the tachycardia rhythm comprises:
   classifying the tachycardia rhythm as ventricular tachycardia if the rate of change in heart rate variability exceeds both a first and second threshold; and
   classifying the tachycardia rhythm as supraventricular tachycardia if the rate of change in heart rate variability does not exceed both the first and second threshold.

2. The method of claim 1, wherein classifying the tachycardia rhythm as supraventricular tachycardia comprises:
   classifying the tachycardia rhythm as sinus tachycardia if the rate of change in heart rate variability does not exceed either of the first and second thresholds; and classifying the tachycardia rhythm as atrial tachycardia if the rate of change in heart rate variability exceeds the first threshold but not the second threshold.

3. The method of claim 1, wherein values of the first and second thresholds are defined based on clinician input.

4. The method of claim 1, further comprising identifying a type of supraventricular tachycardia based on the rate of change in heart rate and rate of change in heart rate variability.

5. A method comprising:
recording heart rate data for a patient over a period of time;
recording heart rate variability data for the patient over the period of time;
identifying a relationship between heart rate and heart rate variability for the patient based on the recorded data;
detecting a tachycardia rhythm of the patient;
identifying a rate of change in heart rate corresponding to the tachycardia rhythm;
identifying a rate of change in heart rate variability corresponding to the tachycardia rhythm; and
classifying the tachycardia rhythm as at least one of supraventricular tachycardia or ventricular tachycardia based on each of the rate of change in heart rate, the rate of change in heart rate variability, and the relationship.

6. A system comprising:
a sensor configured to sense activity of a heart of a patient; and
a processor configured to detect a tachycardia rhythm based on the sensed activity, identify a rate of change in heart rate corresponding to the tachycardia rhythm, identify a rate of change in heart rate variability corresponding to the tachycardia rhythm, and classify the tachycardia rhythm as at least one of supraventricular tachycardia or ventricular tachycardia based on the rate of change in heart rate and rate of change in heart rate variability,
wherein the processor is configured to classify the tachycardia rhythm as ventricular tachycardia if the rate of change in heart rate variability exceeds both a first and second threshold and classify the tachycardia rhythm as supraventricular tachycardia if the rate of change in heart rate variability does not exceed both the first and second threshold.

7. The system of claim 6, wherein the processor is configured to classify the tachycardia rhythm as sinus tachycardia if the rate of change in heart rate variability does not exceed either of the first and second thresholds and classify the tachycardia rhythm as atrial tachycardia if the rate of change in heart rate variability exceeds the first threshold but not the second threshold.

8. The system of claim 6, wherein values of the first and second thresholds are defined based on clinician input.

9. The system of claim 6, wherein the processor is configured to identify a type of supraventricular tachycardia based on the rate of change in heart rate and rate of change in heart rate variability.

10. The system of claim 6, further comprising a medical device, wherein the medical device comprises at least one of the sensor or the processor.

11. The system of claim 10, wherein the medical device comprises an implantable medical device.

12. The system of claim 10, wherein the sensor comprises one or more electrodes coupled to the medical device via one or more leads.

13. A system comprising,
a sensor configured to sense activity of a heart of a patient; and
a processor configured to detect a tachycardia rhythm based on the sensed activity, identify a rate of change in heart rate corresponding to the tachycardia rhythm, identify a rate of change in heart rate variability corresponding to the tachycardia rhythm, and classify the tachycardia rhythm as at least one of supraventricular tachycardia or ventricular tachycardia based on the rate of change in heart rate and rate of change in heart rate variability,
wherein the processor is configured to record heart rate data for the patient over a period of time based on the sensed activity, record heart rate variability data for the patient over the period of time based on the sensed activity, identify a relationship between heart rate and heart rate variability for the patient based on the recorded data, and classify the tachycardia rhythm as at least one of supraventricular tachycardia or ventricular tachycardia based on each of the rate of change in heart rate, rate of change in heart rate variability, and the relationship.

14. A system comprising:
means for detecting a tachycardia rhythm;
means for identifying a rate of change in heart rate corresponding to the tachycardia rhythm;
means for identifying a rate of change in heart rate variability corresponding to the tachycardia rhythm; and
means for classifying the tachycardia rhythm as at least one of supraventricular tachycardia or ventricular tachycardia based on the rate of change in heart rate and rate of change in heart rate variability, wherein the means for classifying the tachycardia rhythm comprises:
means for classifying the tachycardia rhythm as ventricular tachycardia if the rate of change in heart rate variability exceeds both a first and second threshold; and
means for classifying the tachycardia rhythm as supraventricular tachycardia if the rate of change in heart rate variability does not exceed both the first and second threshold.

15. A method comprising:
recording heart rate data for a patient over a period of time;
recording heart rate variability data for the patient over the period of time;
identifying a relationship between heart rate and heart rate variability for the patient based on the recorded data;
subsequently detecting a tachycardia rhythm in the patient; and
classifying the tachycardia rhythm as at least one of supraventricular tachycardia or ventricular tachycardia based on the relationship.

16. The method of claim 15, wherein classifying the tachycardia rhythm comprises classifying the tachycardia rhythm as supraventricular tachycardia or ventricular tachycardia based on whether a heart rate associated with the tachycardia rhythm and a heart rate variability associated with the tachycardia rhythm are within a tolerance value of the relationship.

17. A system comprising:
a sensor configured to sense activity of a heart of a patient; and
a processor configured to record heart rate data for the patient over a period of time based on the sensed activity, record heart rate variability data for the patient over the period of time based on the sensed activity, identify a relationship between heart rate and heart rate variability for the patient based on the recorded data, subsequently detect a tachycardia rhythm in the patient based on the sensed activity, and classify the tachycardia rhythm as at least one of supraventricular tachycardia or ventricular tachycardia based on the relationship.

18. The system of claim 17, wherein the processor is configured to classify the tachycardia rhythm based on whether a heart rate associated with the tachycardia rhythm and a heart rate variability associated with the tachycardia rhythm are within a tolerance value of the relationship.

19. The system of claim 17, further comprising a medical device, wherein the medical device comprises at least one of the sensor or the processor.

20. The system of claim 19, wherein the medical device comprises an implantable medical device.

21. The system of claim 19, wherein the sensor comprises one or more electrodes coupled to the medical device via one or more leads.

22. A system comprising:
means for recording heart rate data for a patient over a period of time;
means for recording heart rate variability data for the patient over the period of time;
means for identifying a relationship between heart rate and heart rate variability for the patient based on the recorded data;
means for subsequently detecting a tachycardia rhythm in the patient; and
means for classifying the tachycardia rhythm as at least one of supraventricular tachycardia or ventricular tachycardia based on the relationship.

* * * * *